(12) United States Patent
Khalaj et al.

(10) Patent No.: US 11,464,485 B2
(45) Date of Patent: Oct. 11, 2022

(54) TRANSDUCER-MOUNTED NEEDLE ASSEMBLY WITH IMPROVED ELECTRICAL CONNECTION TO POWER SOURCE

(71) Applicant: Avent, Inc., Alpharetta, GA (US)

(72) Inventors: Steve S. Khalaj, Laguna Hills, CA (US); Marc Comtois, Irvine, CA (US); Shirzad Shahriari, Irvine, CA (US); Shiva Sharareh, Laguna Niguel, CA (US); Justin J. Coker, Laguna Niguel, CA (US)

(73) Assignee: Avent, Inc., Alpharetta, GA (US)

( * ) Notice: Subject to any disclaimer, the term of this patent is extended or adjusted under 35 U.S.C. 154(b) by 329 days.

(21) Appl. No.: 16/233,595

(22) Filed: Dec. 27, 2018

(65) Prior Publication Data

US 2020/0205779 A1    Jul. 2, 2020

(51) Int. Cl.
*A61B 8/00* (2006.01)
*A61B 8/08* (2006.01)
*A61B 8/12* (2006.01)

(52) U.S. Cl.
CPC ............ *A61B 8/445* (2013.01); *A61B 8/0841* (2013.01); *A61B 8/461* (2013.01); *A61B 8/5223* (2013.01); *A61B 8/56* (2013.01); *A61B 8/12* (2013.01); *A61B 8/4483* (2013.01); *A61B 8/5207* (2013.01)

(58) Field of Classification Search
CPC ....... A61B 8/445; A61B 8/0841; A61B 8/461; A61B 8/5223; A61B 8/56; A61B 8/12; A61B 8/4483; A61B 8/5207; A61B 8/4444; A61B 8/4455; A61B 8/4494
See application file for complete search history.

(56) References Cited

U.S. PATENT DOCUMENTS

| | | | |
|---|---|---|---|
| 4,249,539 | A | 2/1981 | Vilkomerson et al. |
| 4,576,181 | A | 3/1986 | Wallace et al. |
| 5,174,295 | A | 12/1992 | Christian et al. |
| 5,299,571 | A | 4/1994 | Mastrototaro |
| 5,344,435 | A | 9/1994 | Turner et al. |
| 5,354,220 | A | 10/1994 | Ganguly et al. |
| 5,357,955 | A | 10/1994 | Wolf et al. |
| 5,485,845 | A | 1/1996 | Verdonk et al. |

(Continued)

FOREIGN PATENT DOCUMENTS

| EP | 1 568 324 A2 | 8/2005 |
|---|---|---|
| EP | 1 652 471 A1 | 5/2006 |

(Continued)

OTHER PUBLICATIONS

International Search Report and Written Opinion for PCT/US2019/067042, dated Jun. 25, 2020, 17 pages.

*Primary Examiner* — Boniface Ngathi N
(74) *Attorney, Agent, or Firm* — Dority & Manning, P.A.

(57) ABSTRACT

A needle assembly for use with an ultrasound imaging system includes a needle having a proximal end and a distal end. The distal end is adapted to be inserted into a patient. The needle assembly also includes a transducer mounted to an exterior surface of the needle at the distal end. Further, the needle assembly includes a flexible printed circuit board mounted on the exterior surface of the needle from the proximal end to the distal end. As such, the flexible printed circuit board electrically connects the transducer to a power source.

18 Claims, 10 Drawing Sheets

(56) References Cited

U.S. PATENT DOCUMENTS

| | | | |
|---|---|---|---|
| 5,542,915 A | 8/1996 | Edwards et al. | |
| 5,954,649 A | 9/1999 | Chia et al. | |
| 5,989,276 A | 11/1999 | Houser et al. | |
| 6,165,164 A | 12/2000 | Hill et al. | |
| 6,217,518 B1 * | 4/2001 | Holdaway | A61B 5/6848 600/439 |
| 6,554,801 B1 | 4/2003 | Steward et al. | |
| 6,582,368 B2 | 6/2003 | Holdaway et al. | |
| 6,862,468 B2 | 3/2005 | Smith | |
| 6,911,027 B1 | 6/2005 | Edwards et al. | |
| 7,699,829 B2 | 4/2010 | Harris et al. | |
| 7,713,200 B1 | 5/2010 | Sarvazyan et al. | |
| 8,147,414 B2 | 4/2012 | Abraham | |
| 8,167,805 B2 | 5/2012 | Emery et al. | |
| 8,282,565 B2 | 10/2012 | Mahapatra et al. | |
| 8,556,883 B2 | 10/2013 | Saleh | |
| 8,632,468 B2 | 1/2014 | Glossop et al. | |
| 9,179,971 B2 | 11/2015 | Kirschenman | |
| 9,301,690 B2 | 4/2016 | Razavi et al. | |
| 9,326,813 B2 | 5/2016 | Pike, Jr. et al. | |
| 9,445,746 B1 | 9/2016 | Elberse et al. | |
| 9,474,506 B2 | 10/2016 | Magnin et al. | |
| 9,855,021 B2 | 1/2018 | Abraham | |
| 9,972,082 B2 | 5/2018 | Holsing et al. | |
| 2001/0047134 A1 | 11/2001 | Holdaway et al. | |
| 2002/0022833 A1 * | 2/2002 | Maguire | A61B 17/2202 606/27 |
| 2004/0106869 A1 | 6/2004 | Tepper | |
| 2004/0162507 A1 | 8/2004 | Govari | |
| 2006/0079764 A1 * | 4/2006 | Wright | A61B 5/06 600/431 |
| 2006/0135884 A1 | 6/2006 | Hack et al. | |
| 2008/0114309 A1 | 5/2008 | Zuckerman | |
| 2008/0172119 A1 | 7/2008 | Yamasaki et al. | |
| 2009/0069808 A1 | 3/2009 | Pike, Jr. et al. | |
| 2009/0105597 A1 | 4/2009 | Abraham | |
| 2010/0010323 A1 | 1/2010 | Jobst | |
| 2010/0204643 A1 * | 8/2010 | Sarvazyan | A61B 5/06 604/22 |
| 2011/0166455 A1 * | 7/2011 | Cully | A61B 8/4466 600/463 |
| 2011/0184313 A1 * | 7/2011 | Gianchandani | A61B 18/082 600/567 |
| 2012/0287750 A1 | 11/2012 | Deladi et al. | |
| 2013/0109974 A1 | 5/2013 | Nishina et al. | |
| 2013/0158459 A1 | 6/2013 | Goedje et al. | |
| 2013/0261467 A1 | 10/2013 | Dausch et al. | |
| 2014/0024911 A1 | 1/2014 | Harley et al. | |
| 2014/0121502 A1 | 5/2014 | Vignon et al. | |
| 2014/0171788 A1 | 6/2014 | Stigall | |
| 2014/0275810 A1 | 9/2014 | Keller et al. | |
| 2014/0316269 A1 | 10/2014 | Zhang et al. | |
| 2015/0201994 A1 | 7/2015 | Vetter | |
| 2015/0351645 A1 | 12/2015 | Hiltner | |
| 2016/0045184 A1 | 2/2016 | Courtney et al. | |
| 2016/0066987 A1 | 3/2016 | Budzelaar et al. | |
| 2016/0158509 A1 | 6/2016 | Wedan et al. | |
| 2017/0000980 A1 | 1/2017 | Potosky | |
| 2017/0020422 A1 | 1/2017 | Bigelow et al. | |
| 2017/0020562 A1 | 1/2017 | Erkamp et al. | |
| 2017/0027605 A1 | 2/2017 | Erkamp et al. | |
| 2017/0033474 A1 | 2/2017 | Erkamp et al. | |
| 2017/0172544 A1 | 6/2017 | Erkamp et al. | |
| 2017/0196591 A1 | 7/2017 | Long, Jr. et al. | |
| 2018/0036513 A1 | 2/2018 | Cruz, Jr. et al. | |
| 2018/0064415 A1 | 3/2018 | Zhai et al. | |
| 2018/0078170 A1 | 3/2018 | Panescu et al. | |
| 2018/0085519 A1 | 3/2018 | McCaffrey et al. | |
| 2018/0116629 A1 | 5/2018 | Boctor et al. | |
| 2018/0132754 A1 | 5/2018 | Kusumoto | |
| 2018/0132945 A1 | 5/2018 | Fazzi | |
| 2018/0146981 A1 | 5/2018 | De Wijs et al. | |

FOREIGN PATENT DOCUMENTS

| | | | | |
|---|---|---|---|---|
| GB | 2 423 255 A | | 8/2006 | |
| JP | 3461584 B2 | * | 10/2003 | |
| KR | 20120061340 A | | 6/2012 | |
| WO | WO 89/09633 | | 10/1989 | |
| WO | WO-2014062512 A1 | * | 4/2014 | A61B 8/12 |
| WO | WO 2014/139005 A1 | | 9/2014 | |
| WO | WO-2015155630 A1 | * | 10/2015 | A61B 8/0841 |
| WO | WO-2015155644 A1 | * | 10/2015 | A61B 8/4438 |
| WO | WO-2015155645 A1 | * | 10/2015 | A61B 8/4494 |
| WO | WO 2016/160712 A1 | | 10/2016 | |
| WO | WO 2018/116114 A1 | | 6/2018 | |

* cited by examiner

TRANSDUCER-MOUNTED NEEDLE ASSEMBLY WITH IMPROVED ELECTRICAL CONNECTION TO POWER SOURCE

FIELD OF THE INVENTION

The present invention relates generally to needle assemblies for use in nerve block procedures, and more particularly, to a needle assembly with improved electrical connection to a power source.

BACKGROUND

Detection of anatomical objects using medical imaging is an essential step for many medical procedures, such as regional anesthesia nerve blocks, and is becoming the standard in clinical practice to support diagnosis, patient stratification, therapy planning, intervention, and/or follow-up. Various systems based on traditional approaches exist for anatomical detection and tracking in medical images, such as computed tomography (CT), magnetic resonance (MR), ultrasound, and fluoroscopic images.

For example, ultrasound imaging systems utilize sound waves with frequencies higher than the upper audible limit of human hearing. Further, ultrasound imaging systems are widely used in medicine to perform both diagnosis and therapeutic procedures. In such procedures, sonographers perform scans of a patient using a hand-held probe or transducer that is placed directly on and moved over the patient.

Certain ultrasound systems may be used in combination with needles having active (i.e. electrically-powered) transducers, which require an electrical connection to a power source. Such needle assemblies typically route cabling from the power source through a lumen of the needle and to the transducer. However, when the cabling is routed through the needle lumen, a portion of the internal diameter of the needle is obstructed, thereby preventing fluid/medicine from flowing freely therethrough.

Accordingly, the present disclosure is directed to a needle assembly with improved electrical connection to a power source that addresses the aforementioned issues.

SUMMARY OF THE INVENTION

Objects and advantages of the invention will be set forth in part in the following description, or may be obvious from the description, or may be learned through practice of the invention.

In one aspect, the present invention is directed to a needle assembly for an ultrasound imaging system. The needle assembly includes a needle having a proximal end and a distal end. The distal end is adapted to be inserted into a patient. The needle assembly also includes a transducer mounted to an exterior surface of the needle at the distal end. Further, the needle assembly includes a flexible printed circuit board mounted on the exterior surface of the needle from the proximal end to the distal end. As such, the flexible printed circuit board electrically connects the transducer to a power source.

In one embodiment, the flexible printed circuit board may include, for example, a plurality of electronic components and conductive tracks printed on the exterior surface of needle. For example, in certain embodiments, the electronic components and conductive tracks may be printed on the exterior surface of needle via screen printing, flexography, gravure printing, offset lithography, inkjet printing, or any other suitable printing process.

In another embodiment, the needle assembly may also include at least one insulation layer positioned atop the flexible printed circuit board opposite the exterior surface of the needle so as to shield the flexible printed circuit board from the patient. In addition, the needle assembly may include at least one insulation layer positioned between the flexible printed circuit board and the exterior surface of the needle.

In further embodiments, the electronic components and the conductive tracks of the flexible printed circuit board may be arranged linearly from the proximal end to the distal end of the needle. In alternative embodiments, the electronic components and the conductive tracks of the flexible printed circuit board may be arranged in a helical pattern from the proximal end to the distal end of the needle.

In another aspect, the present disclosure is directed to a needle assembly for use with an ultrasound imaging system. The needle assembly includes a needle having a proximal end and a distal end. The distal end is adapted to be inserted into a patient. The needle assembly also includes a needle transducer mounted to an exterior surface of the needle at the distal end. Further, the needle assembly includes a conduit assembly secured to an exterior surface of the needle from the proximal end to the distal end. Further, the conduit assembly defines at least one lumen therethrough. As such, the needle assembly also includes at least one electrically-conductive cable extending through the conduit assembly and electrically connecting the needle transducer to a power source.

In one embodiment, the conduit assembly may be constructed of metal tubing, polymer shrink tubing, or any other suitable tubing material. In another embodiment, the conduit assembly may define at least two lumens.

In further embodiments, the conduit assembly may be arranged linearly from the proximal end to the distal end of the needle. In alternative embodiments, the conduit assembly may be arranged in a helical pattern from the proximal end to the distal end of the needle.

In additional embodiments, the electrically-conductive cable(s) may include a single core wire, a coaxial cable, or any other suitable cable or wire.

In yet another aspect, the present disclosure is directed to a needle assembly for use with an ultrasound imaging system. The needle assembly includes a needle having a proximal end and a distal end. The distal end is adapted to be inserted into a patient. The needle assembly also includes a needle transducer mounted to an exterior surface of the needle at the distal end. Further, the needle assembly includes at least one electrical trace printed on the exterior surface of the needle from the proximal end to the distal end via an additive manufacturing process. As such, the electrical trace(s) electrically connects the needle transducer to a power source.

In one embodiment, the needle assembly may include a plurality of electrical traces printed on the exterior surface of needle via the additive manufacturing process. Further, in certain embodiments, the additive manufacturing process may include, for example, of directed energy deposition, direct laser deposition, or any other suitable additive manufacturing technique.

In another embodiment, the needle assembly may include at least one insulation layer positioned atop the electrical trace(s) opposite the exterior surface of the needle so as to shield the at least one electrical trace from the patient. In addition, the needle assembly may include at least one insulation layer positioned between the electrical trace(s) and the exterior surface of the needle.

In further embodiments, the electrical trace(s) may be arranged linearly from the proximal end to the distal end of the needle. In alternative embodiments, the electrical trace(s) may be arranged in a helical pattern from the proximal end to the distal end of the needle.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Figure 1:
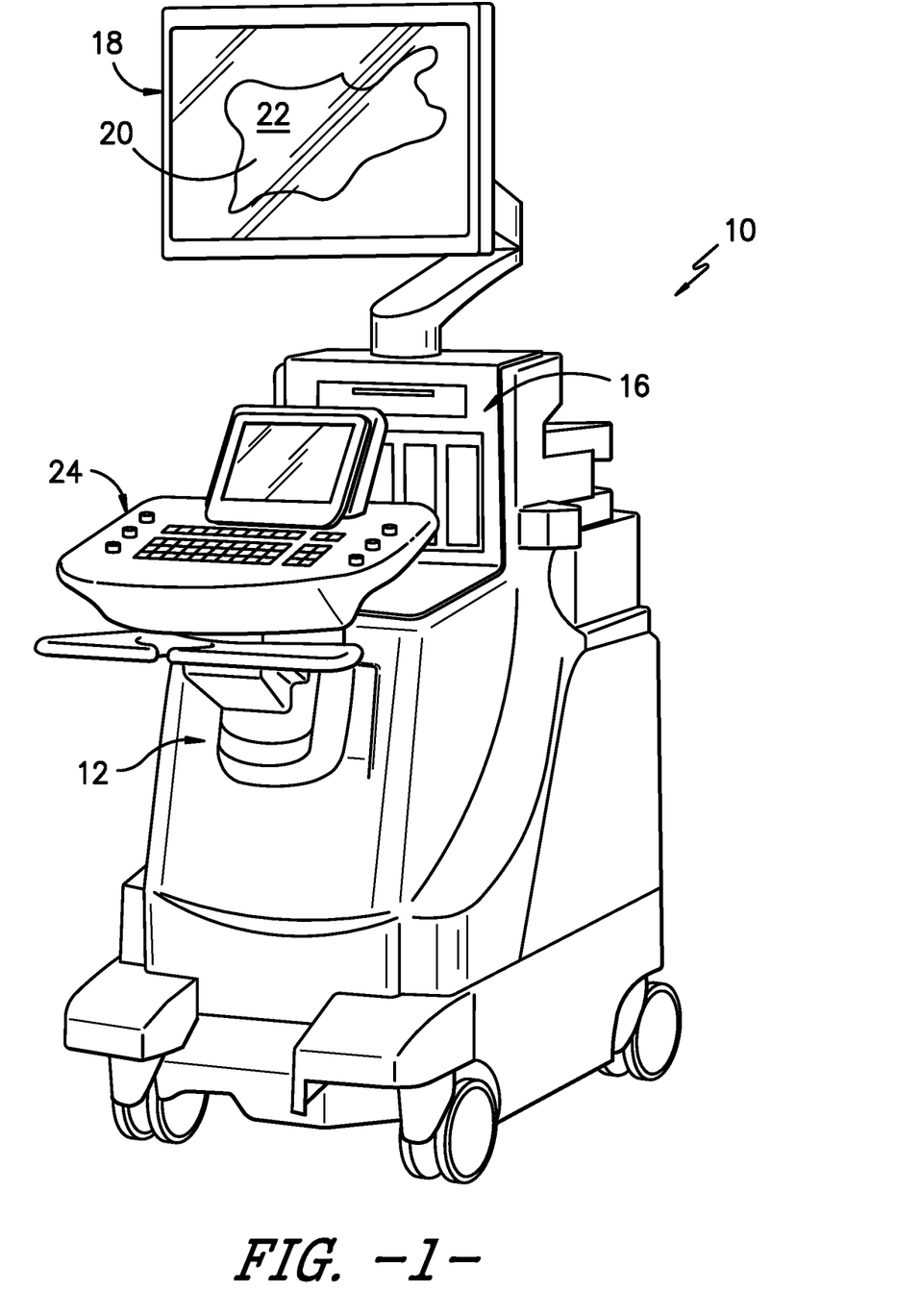
FIG. 1 illustrates a perspective view of one embodiment of an imaging system according to the present disclosure.
Figure 2:
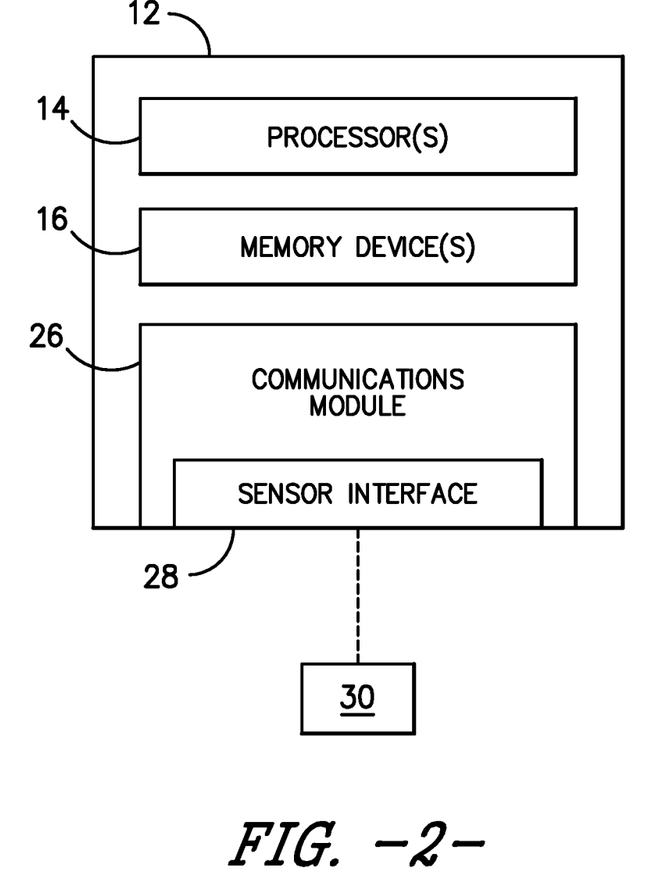
FIG. 2 illustrates a block diagram one of embodiment of a controller of an imaging system according to the present disclosure.

Referring now to the drawings, FIGS. 1 and 2 illustrate a medical imaging system 10 for scanning, identifying, and navigating anatomical objects of a patient according to the present disclosure. As used herein, the anatomical object(s) 22 and surrounding tissue described herein may include any anatomical structure and/or surrounding tissue of a patient. For example, in one embodiment, the anatomical object(s) 22 may include one or more nerves or nerve bundles. More specifically, in another embodiment, the anatomical object(s) 22 may include an interscalene brachial plexus of the patient, which generally corresponds to the network of nerves running from the spine, formed by the anterior rami of the lower four cervical nerves and first thoracic nerve. As such, the surrounding tissue of the brachial plexus generally corresponds to the sternocleidomastoid muscle, the middle scalene muscle, the anterior scalene muscle, and/or similar.

It should be understood, however, that the system of the present disclosure may be further used for any variety of medical procedures involving any anatomical structure in addition to those relating to the brachial plexus. For example, the anatomical object(s) 22 may include upper and lower extremities, as well as compartment blocks. More specifically, in such embodiments, the anatomical object(s) 22 of the upper extremities may include interscalene muscle, supraclavicular muscle, infraclavicular muscle, and/or axillary muscle nerve blocks, which all block the brachial plexus (a bundle of nerves to the upper extremity), but at different locations. Further, the anatomical object(s) 22 of the lower extremities may include the lumbar plexus, the fascia Iliac, the femoral nerve, the sciatic nerve, the abductor canal, the popliteal, the saphenous (ankle), and/or similar. In addition, the anatomical object(s) 22 of the compartment blocks may include the intercostal space, transversus abdominis plane, and thoracic paravertebral space, and/or similar.

In addition, as shown, the imaging system 10 may correspond to an ultrasound imaging system or any other suitable imaging system that can benefit from the present technology. Thus, as shown, the imaging system 10 may generally include a controller 12 having one or more processor(s) 14 and associated memory device(s) 16 configured to perform a variety of computer-implemented functions (e.g., performing the methods and the like and storing relevant data as disclosed herein), as well as a user display 18 configured to display an image 20 of an anatomical object 22 or the surrounding tissue to an operator. In addition, the imaging system 10 may include a user interface 24, such as a computer and/or keyboard, configured to assist a user in generating and/or manipulating the user display 18.

Additionally, as shown in FIG. 2, the processor(s) 14 may also include a communications module 26 to facilitate communications between the processor(s) 14 and the various components of the imaging system 10, e.g. any of the components of FIG. 1. Further, the communications module 26 may include a sensor interface 28 (e.g., one or more analog-to-digital converters) to permit signals transmitted from one or more probes (e.g. such as an ultrasound transducer and/or a needle transducer 30 as described herein) to be converted into signals that can be understood and processed by the processor(s) 14.

It should be appreciated that the various probes and/or transducers described herein may be communicatively coupled to the communications module 26 of the controller 12 using any suitable means. For example, as shown in FIG. 2, the needle transducer 30 may be coupled to the sensor interface 28 via a wired connection. However, in other embodiments, the needle transducer 30 may be coupled to the sensor interface 28 via a wireless connection, such as by using any suitable wireless communications protocol known in the art. As such, the processor(s) 14 may be configured to receive one or more sensor signals from the needle transducer 30.

As used herein, the term "processor" refers not only to integrated circuits referred to in the art as being included in a computer, but also refers to a controller, a microcontroller, a microcomputer, a programmable logic controller (PLC), an application specific integrated circuit, a field-programmable gate array (FPGA), an Application-Specific Integrated Circuit (ASIC), and other programmable circuits. The processor(s) 14 is also configured to compute advanced control algorithms and communicate to a variety of Ethernet or serial-based protocols (Modbus, OPC, CAN, etc.). Furthermore, in certain embodiments, the processor(s) 14 may communicate with a server through the Internet for cloud computing in order to reduce the computation time and burden on the local device. Additionally, the memory device(s) 16 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 16 may generally be configured to store suitable computer-readable instructions that, when implemented by the processor(s) 14, configure the processor(s) 14 to perform the various functions as described herein.

Figure 3:
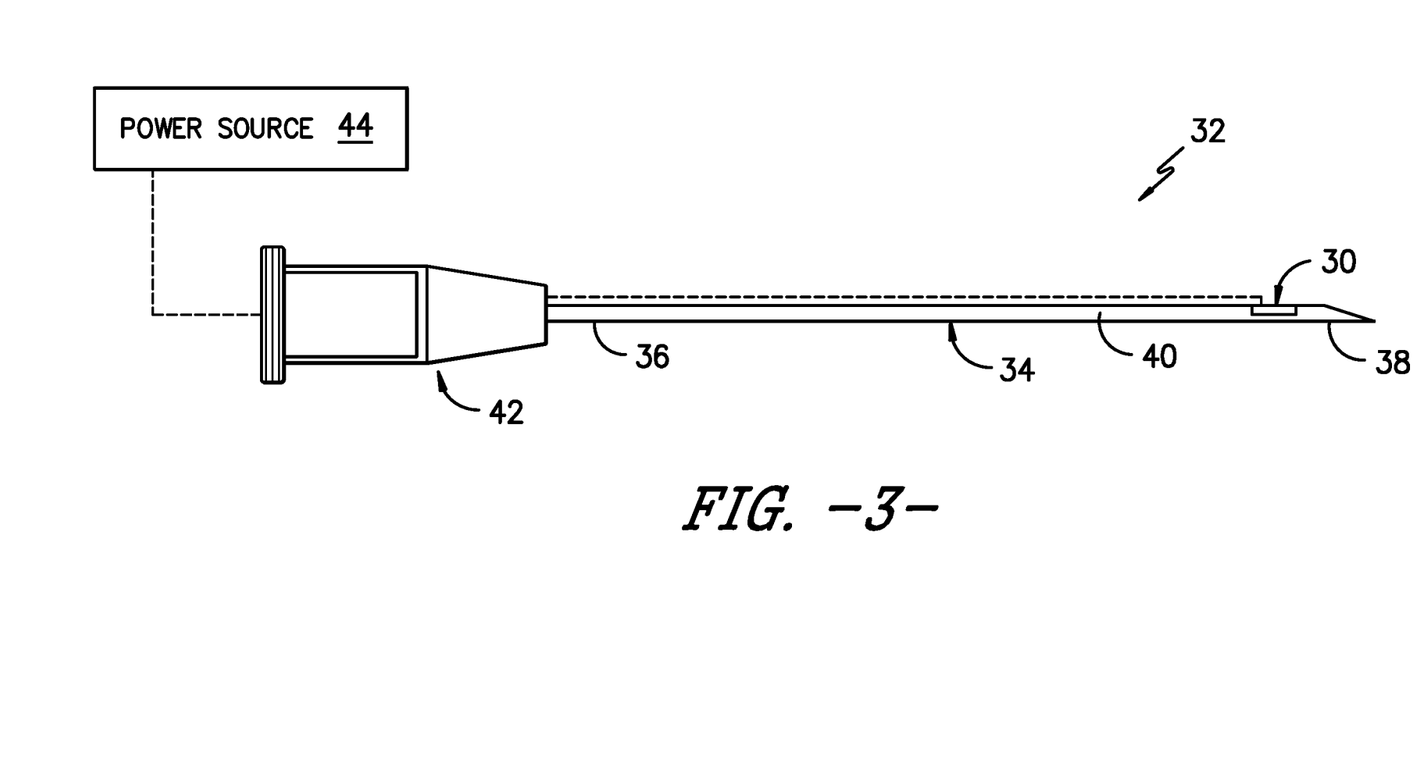
FIG. 3 illustrates a schematic diagram of one embodiment of a needle assembly according to the present disclosure.

Referring now to FIGS. 3-17, various views of embodiments of the present disclosure are provided to illustrate multiple techniques for electrically connecting an electrical device (such as the needle transducer 30) of a needle to a power source (also referred to as a connector) in order to transfer transducer signals of any kind (e.g. current signals) to the connector. Referring particularly to FIG. 3, a side view of one embodiment of the needle assembly 32 for the ultrasound imaging system 10 according to the present disclosure, particularly illustrating an electrical connection between a power source and the needle transducer 30. More specifically, as shown, the needle assembly 32 includes a needle 34 having a proximal end 36 and a distal end 38 adapted to be inserted into a patient and the needle transducer 30, which may be mounted to an exterior surface 40 of the needle 34 at the distal end 38 thereof.

Figure 9:
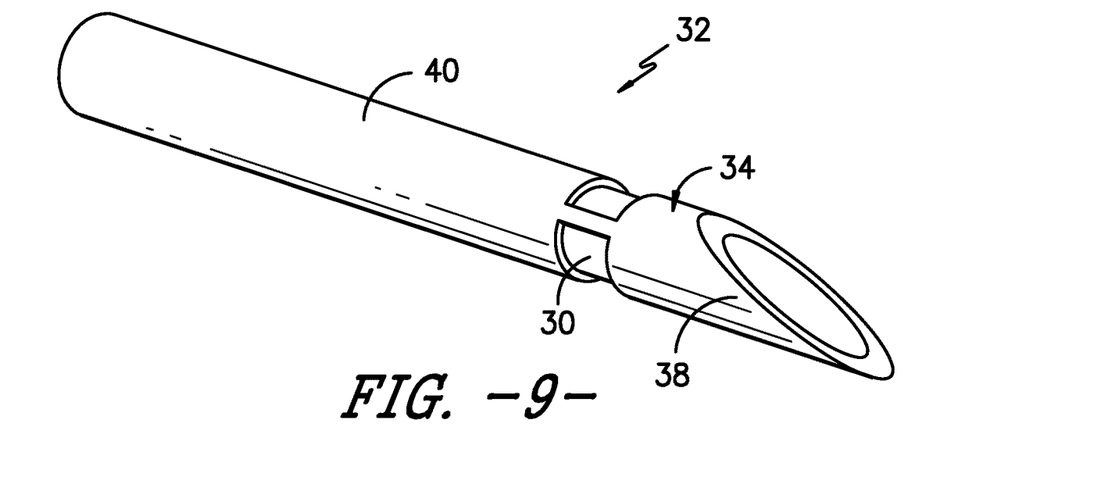
FIG. 9 illustrates a perspective view of a portion of still another embodiment of a distal end of needle assembly according to the present disclosure, particularly illustrating a plurality of needle transducers radially spaced around a circumference of the needle.
Figure 10:
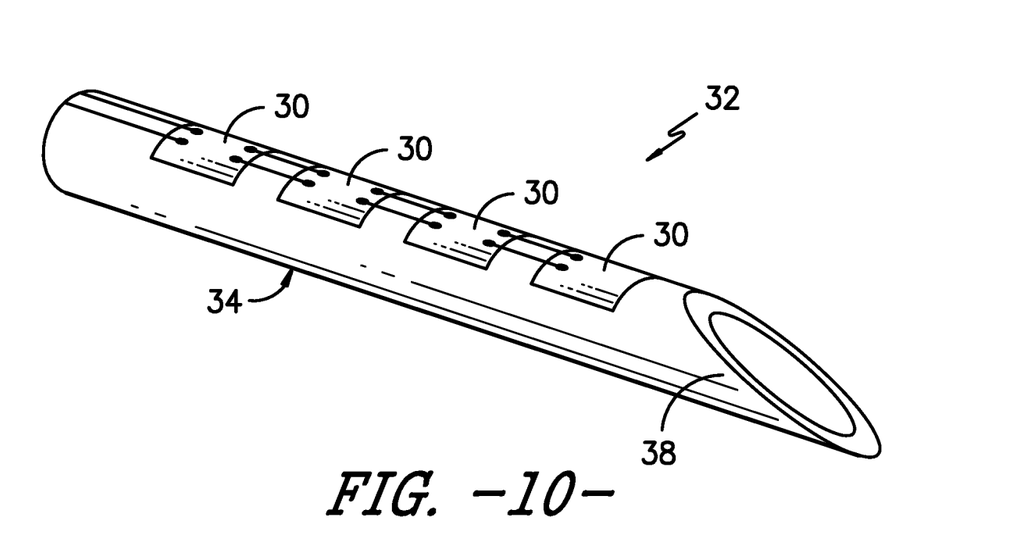
FIG. 10 illustrates a perspective view of a portion of yet another embodiment of a distal end of needle assembly according to the present disclosure, particularly illustrating a plurality of needle transducers mounted along a length of the needle.

It should be understood, however, that the needle transducer 30 may be mounted at any suitable location on the needle 34. In addition, as shown in FIGS. 3, 7, 8, and 10-11, the needle transducer 30 may be mounted on one side of the needle 34. In such embodiments, during operation, the user of the needle assembly 32 must orient the needle transducer 30 towards the ultrasound probe of the ultrasound imaging system 10. In another embodiment, as shown in FIG. 10, the needle assembly 32 may include a plurality of needle transducers 30 spaced along the length of the needle 34. In alternative embodiments, as shown in FIG. 9, the needle assembly 32 may include multiple needle transducers 30 spaced radially around the needle 34. In such embodiments, orientation of the needle 34 is not relevant (i.e. the needle assembly 32 is not direction sensitive) as the ultrasound probe can easily view one of the radially spaced transducers 30 due to the various radial positions.

Further, as shown, the needle 34 may also include a needle hub 42 at its proximal end 36. In such embodiments, the needle transducer(s) 30 may be communicatively coupled to the controller 12 via the needle hub 42. Moreover, the needle transducer(s) 30 may also be coupled to a power source 44 that provides electrical power to the transducer(s) 30. In certain embodiments, the power source 44 may be part of the ultrasound imaging system 10 or may be separate component such that the needle assembly 32 is completely autonomous from the ultrasound imaging system 10.

In addition, the needle transducer(s) 30 may be any suitable transducer now known or later developed in the art. For example, in one embodiment, the transducer(s) 30 may be a piezoelectric (PZT) transducer. Alternatively, the transducer(s) 30 may be a capacitive micromachined ultrasonic (CMUT) transducer. In yet another embodiment, the transducer(s) 30 may also include Polydimethylsiloxane (PDMS) transducers and/or photoacoustic transducers.

Figure 4A:
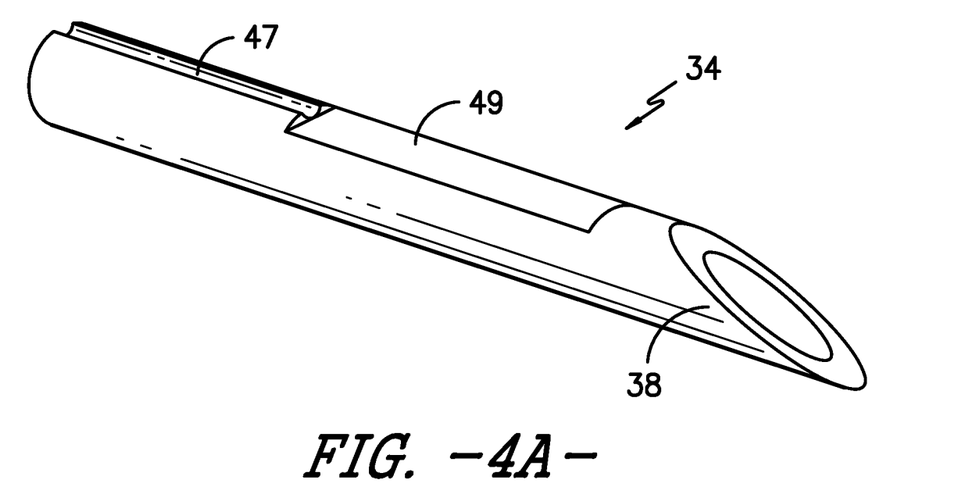
FIG. 4A illustrates a perspective view of one embodiment of a distal end of a needle assembly according to the present disclosure, particularly illustrating the location for a transducer and corresponding wire on an embedded flat portion on the needle.
Figure 4B:
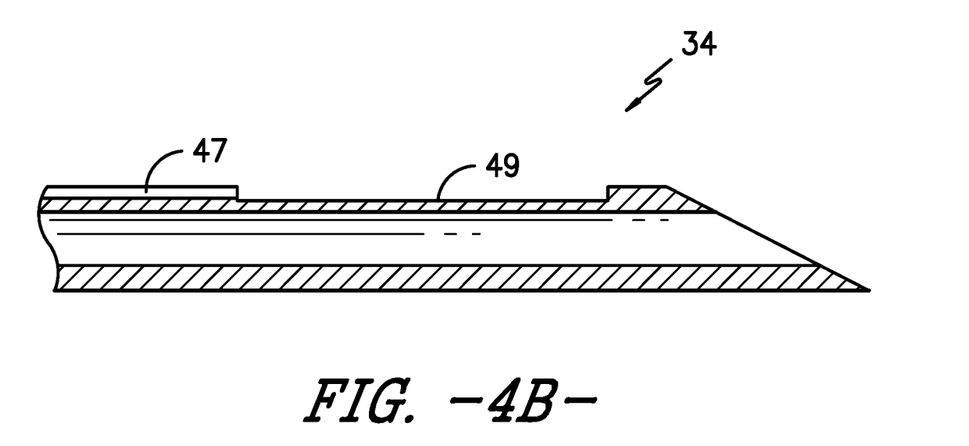
FIG. 4B illustrates a cross-sectional view of the needle assembly of FIG. 4A.
Figure 5A:
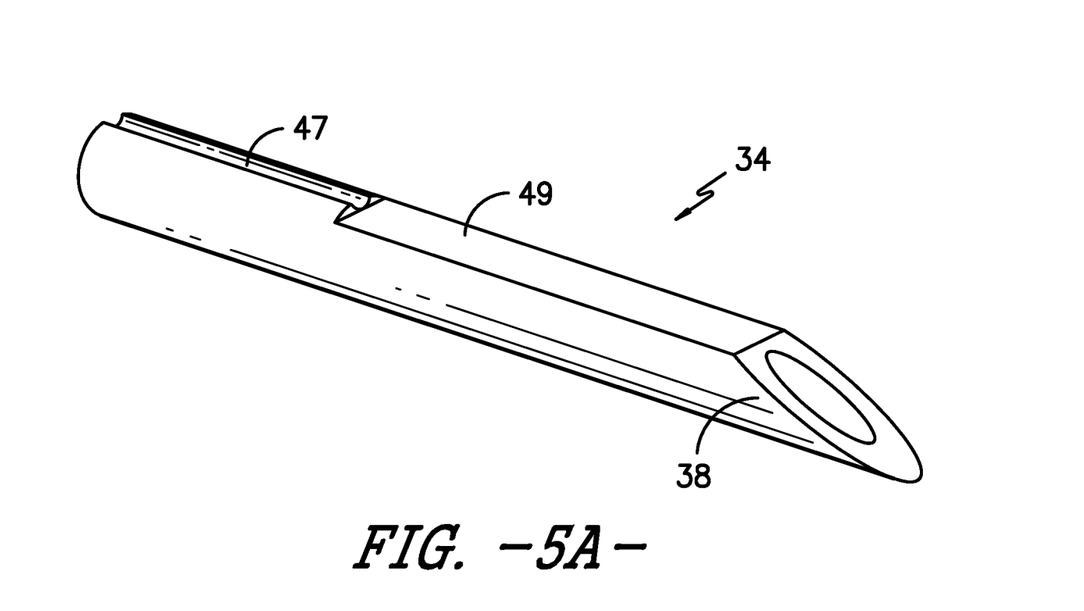
FIG. 5A illustrates a perspective view of one embodiment of a distal end of a needle assembly according to the present disclosure, particularly illustrating the location for a transducer and corresponding wire on a flat portion of the needle that extends to the distal end thereof.
Figure 5B:
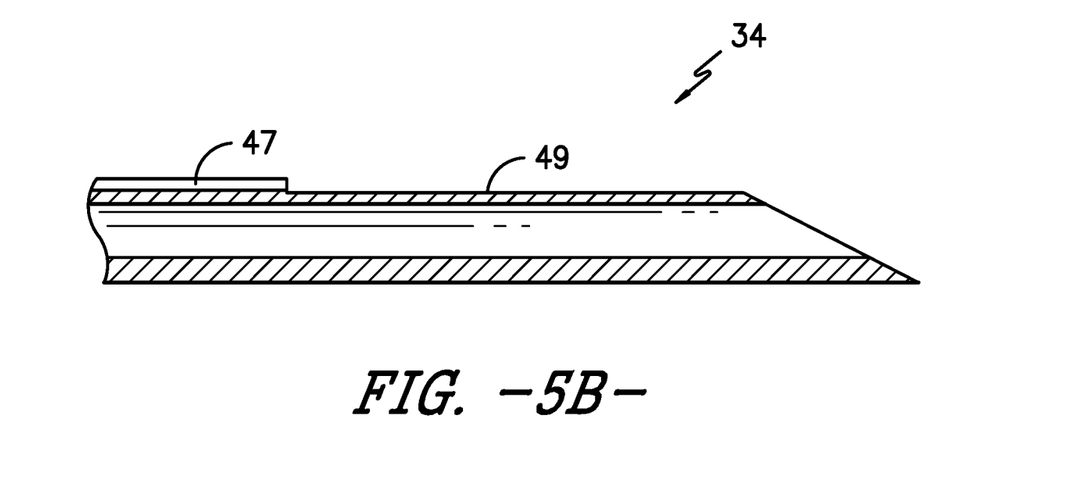
FIG. 5B illustrates a cross-sectional view of the needle assembly of FIG. 5A.
Figure 6A:
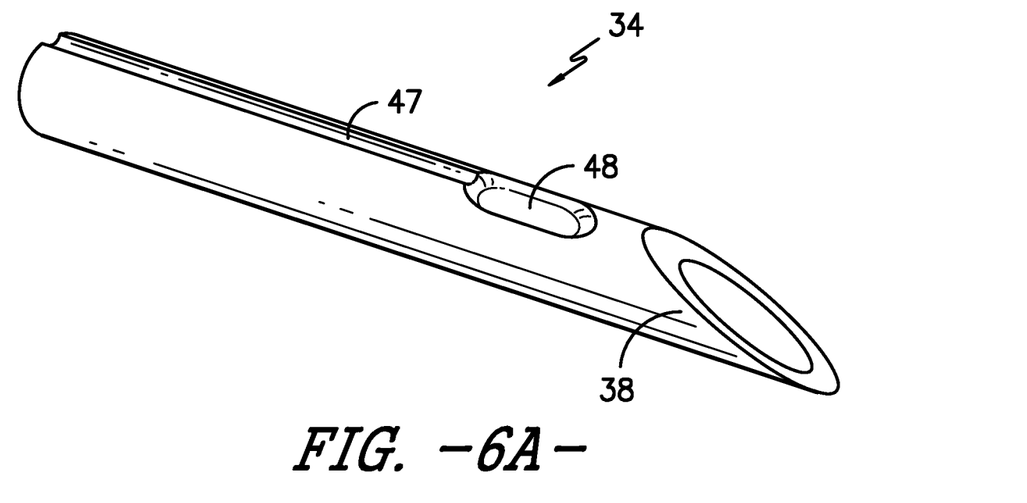
FIG. 6A illustrates a perspective view of one embodiment of a distal end of a needle assembly according to the present disclosure, particularly illustrating the location for a transducer and corresponding wire within a longitudinal groove and recess formed on the body of the needle.
Figure 6B:
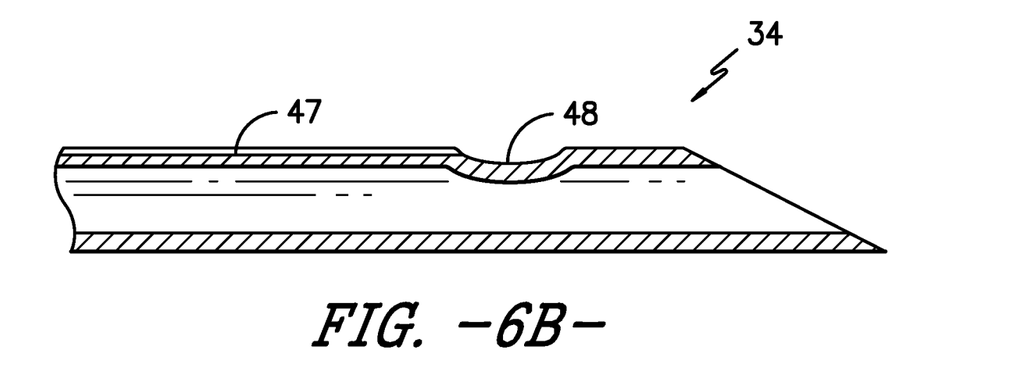
FIG. 6B illustrates a cross-sectional view of one embodiment of the recess of FIG. 6A, particularly illustrating the recess formed such that it intersects with the lumen of the needle.
Figure 6C:
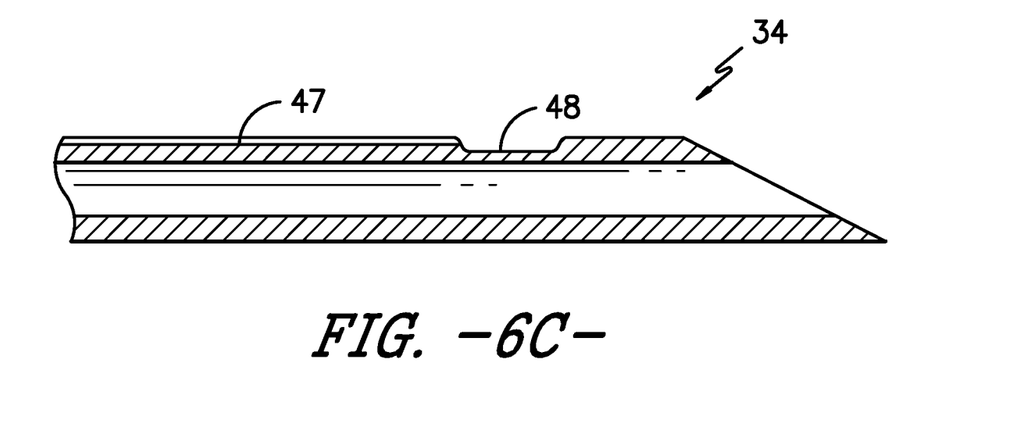
FIG. 6C illustrates a cross-sectional view of another embodiment of the recess of FIG. 5A, particularly illustrating the recess formed in the needle wall such that it does not intersect with the lumen of the needle.

Referring particularly to FIGS. 4A, 4B, 5A, 5B, 6A, 6B, and 6C, various views of different embodiments of the needle 34 of the needle assembly 32 are illustrated. More specifically, FIGS. 4A and 4B illustrate a perspective view and a cross-sectional view of one embodiment of the distal end 38 of the needle 34 according to the present disclosure, particularly illustrating the location for one of the transducers 30 and corresponding traces or wires within an embedded flat portion 49 within the needle wall and a recess extending therefrom, respectively. In such embodiments, the front portion of the needle wall (which allows the needle transducer 30 to be embedded therein) is configured to protect the needle transducer 30 at the time of insertion within a patient. FIGS. 5A and 5B illustrate a perspective view and a cross-sectional view of one embodiment of the distal end 38 of the needle 34 according to the present disclosure, particularly illustrating the location for one of the transducers 30 and the corresponding wire(s) on a flat portion 49 of the needle 34 that extends up to the distal end 38 thereof. Alternatively, FIG. 6A illustrates a perspective view of one embodiment of the distal end 38 of the needle 34 according to the present disclosure, particularly illustrating the location for one of the transducers 30 and one or more corresponding wires within a longitudinal groove 47 and recess 48, respectively, that are formed on the body of the needle 34. In addition, FIG. 6B illustrates a cross-sectional view of one embodiment of the recess 48 of FIG. 6A, particularly illustrating the recess 48 formed such that it intersects with the lumen of the needle 34. Alternatively, as shown in FIG. 6C, a cross-sectional view of another embodiment of the recess 48 of FIG. 6A is illustrated, particularly illustrating the recess 48 formed in the needle wall such that it does not intersect with the lumen of the needle 34.

Figure 7:
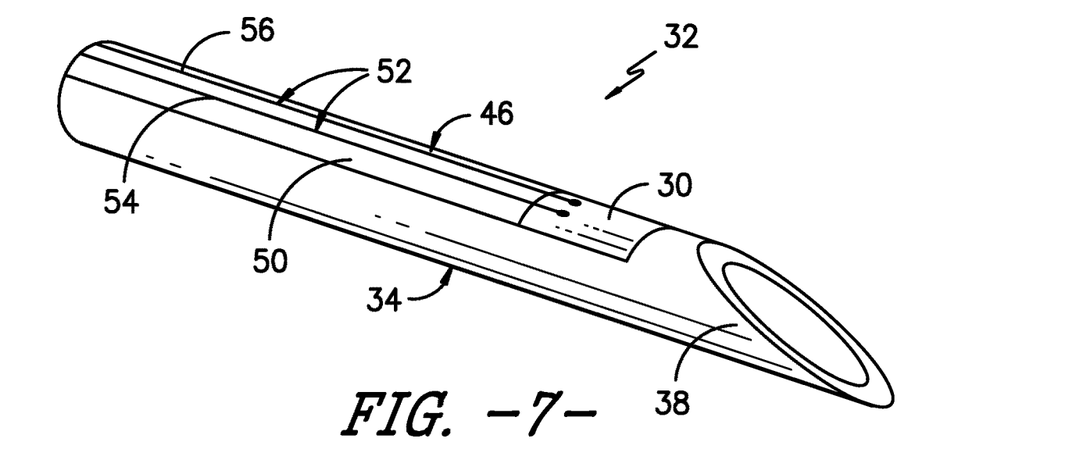
FIG. 7 illustrates a perspective view of a portion of one embodiment of a distal end of needle assembly according to the present disclosure, particularly illustrating a flexible printed circuit board mounted onto an exterior surface of the needle so as to electrically connect a needle transducer at the distal end of the needle to a power source.
Figure 8:
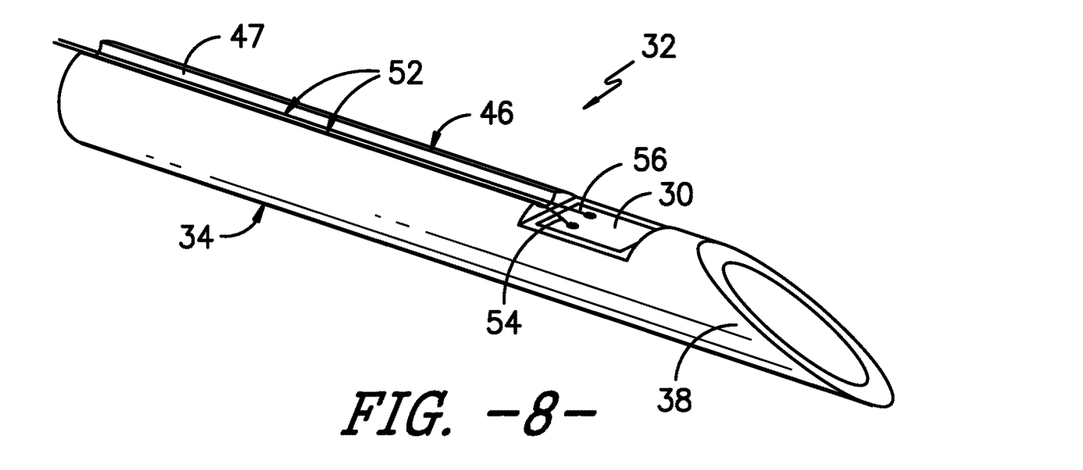
FIG. 8 illustrates a perspective view of a portion of another embodiment of a distal end of needle assembly according to the present disclosure, particularly illustrating a flexible printed circuit board mounted with a recess of the needle so as to electrically connect a needle transducer at the distal end to a power source.

Referring now to FIGS. 7 and 8, detailed views of several embodiments of the needle assembly 32 for use with the ultrasound imaging system 10 according to the present disclosure, particularly illustrating a flexible printed circuit board 46 being utilized to electrically connect the power source 44 and the transducer 30 are illustrated. More specifically, as shown, the flexible printed circuit board 46 is mounted on the exterior surface 40 of the needle 34 and extends from the proximal end 36 to the distal end 38. Thus, as shown, the flexible printed circuit board 46 electrically connects the transducer 30 to the power source 44.

In one embodiment, as shown in each of FIGS. 7 and 8, the flexible printed circuit board 46 may include, for example, a flexible base 50 having one or more conductive tracks 52 or traces printed thereon. As such, the flexible base 50 can easily flex with the shape of the needle 34 so as to be effectively mounted onto the exterior surface 40 of needle 34. For example, in certain embodiments, the conductive tracks or traces 52 may be printed onto the flexible base 50 via screen printing, flexography, gravure printing, offset lithography, inkjet printing, additive manufacturing, or any other suitable printing process. In addition, in such embodiments, the conductive tracks 52 may be narrow, such as from about 0.10 millimeter (mm) up to about 0.25 mm. Further, in certain embodiments, ground planes can be used to enclose the signal trace to achieve better noise immunity. In addition, as shown, the plurality of conductive tracks 52 may include a first conductive track 54 configured to send signals from the needle transducer 30 and a second conductive track 56 configured to receive signals from the ultrasound imaging system 10.

In addition, as shown in FIG. 8, the illustrated embodiment of the needle assembly 32 includes the recess 47 described herein for receiving the conductive traces 54, 56 as well as an embedded flat recessed portion 49 that receives the needle transducer 30. Further, as shown in FIGS. 4A, 4B, and 8, the flat portion 49 may stop short of the distal-most end of the needle 34 so as to provide further protection to the transducer 30. In alternative embodiments, rather than having two conductive tracks for sending and receiving, the needle assembly 32 may include a single conductive track to provide a first send/receive path and the needle 34 may act as the second path. In such embodiments, the needle may be split such that the conductive track is mounted to a first side of the needle 34 and the opposing split side provides the second path. Alternatively, the conductive track may simply be isolated from another portion of the needle 34.

Figure 11:
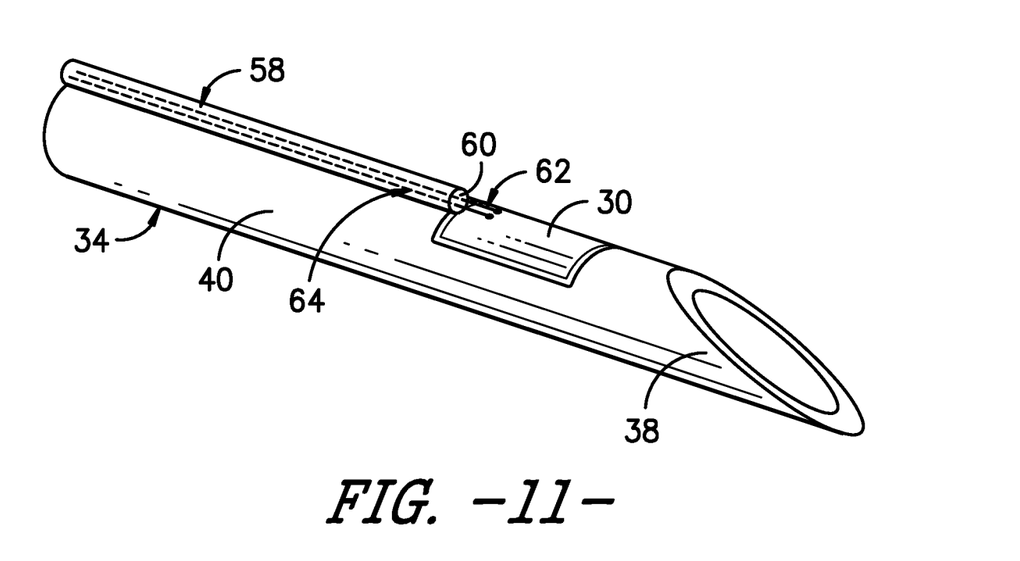
FIG. 11 illustrates a perspective view of another embodiment of a distal end of a needle assembly according to the present disclosure, particularly illustrating a conduit assembly mounted onto an exterior surface of the needle so as to electrically connect a needle transducer at the distal end to a power source.
Figure 12:
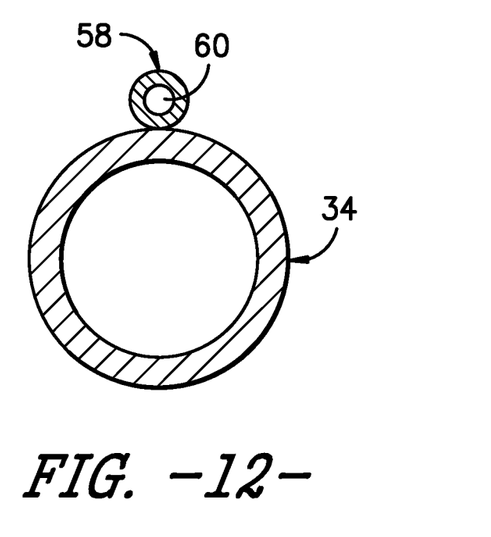
FIG. 12 illustrates a cross-sectional view of the needle assembly of FIG. 7, particularly illustrating a single-lumen conduit assembly mounted onto an exterior surface of the needle.
Figure 13:
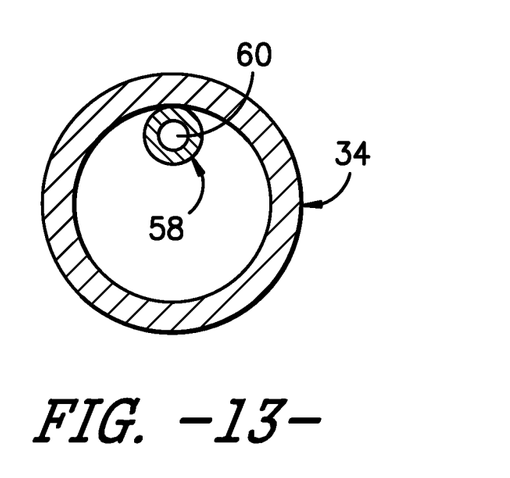
FIG. 13 illustrates a cross-sectional view of another embodiment of the needle assembly according to the present disclosure, particularly illustrating a single-lumen conduit assembly mounted onto an interior surface of the needle.
Figure 14:
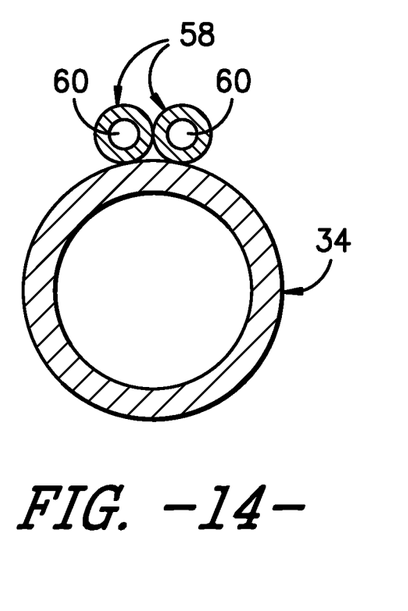
FIG. 14 illustrates a cross-sectional view of another embodiment of the needle assembly according to the present disclosure, particularly illustrating a double-lumen conduit assembly mounted onto an exterior surface of the needle.

Referring particularly to FIGS. 11-14, various views of another embodiment of a needle assembly 32 for use with the ultrasound imaging system 10 according the present disclosure are illustrated. FIG. 11 illustrates a perspective view of another embodiment of the needle assembly 32 for use with the ultrasound imaging system 10 according to the present disclosure. FIG. 12 illustrates a detailed, cross-sectional view of one embodiment of the needle assembly 32 for use with the ultrasound imaging system 10 according to the present disclosure, particularly illustrating a single lumen on the exterior of the lumen 60. FIG. 13 illustrates a detailed, cross-sectional view of another embodiment of the needle assembly 32 for use with the ultrasound imaging system 10 according to the present disclosure, particularly illustrating a single lumen on the interior of the lumen 60. FIG. 14 illustrates yet another detailed, cross-sectional view of one embodiment of the needle assembly 32 for use with the ultrasound imaging system 10 according to the present disclosure, particularly illustrating a double lumen on the exterior of the lumen 60.

As shown in FIG. 11, rather than utilizing the flexible printed circuit board 46, the needle assembly 32 may include a conduit assembly 58 secured to the exterior surface 40 of the needle 34 from the proximal end 36 to the distal end 38. Further, as shown in FIG. 12, the conduit assembly 58 defines at least one lumen 60 therethrough. As such, the needle assembly 32 may also include at least one electrically-conductive cable 62, 64 extending through the conduit assembly 58 so as to electrically connect the needle transducer 30 to the power source 44 of the ultrasound imaging system 10. For example, as shown, the needle assembly 32 includes a first electrically-conductive cable 62 configured to send signals from the needle transducer 30 and a second electrically-conductive cable 64 configured to receive signals from the ultrasound imaging system 10.

In such embodiments, the conduit assembly 58 may be constructed of metal tubing, polymer shrink tubing, or any other suitable tubing material. In addition, in certain embodiments, as shown in FIGS. 12 and 13, the conduit assembly 58 may define a single lumen 60. In addition, as shown, the conduit assembly 58 may be located on the outside of the lumen 60 (FIG. 12) or on the inside of the lumen 60 (FIG. 13). In alternative embodiments, as shown in FIG. 14, the conduit assembly 58 may define at least two lumens 60.

In additional embodiments, the electrically-conductive cable(s) 62, 64 may include a single core wire, a coaxial cable, or any other suitable cable or wire. For example, in one embodiment, the electrically-conductive cable(s) 62, 64 may include a solid- or multi-strand wire, such as an insulated wire of a small gauge (e.g. in the order of 40 AWG or smaller). In another embodiment, the electrically-conductive cable(s) 62, 64 may include a coaxial cable of a small gauge (e.g. in the order of 40 AWG or smaller) so as to provide a better noise immunity environment. In such embodiments, the lumen 60 of the conduit assembly 58 may be up to about 0.5 mm, such as about 0.25 mm.

Figure 15:
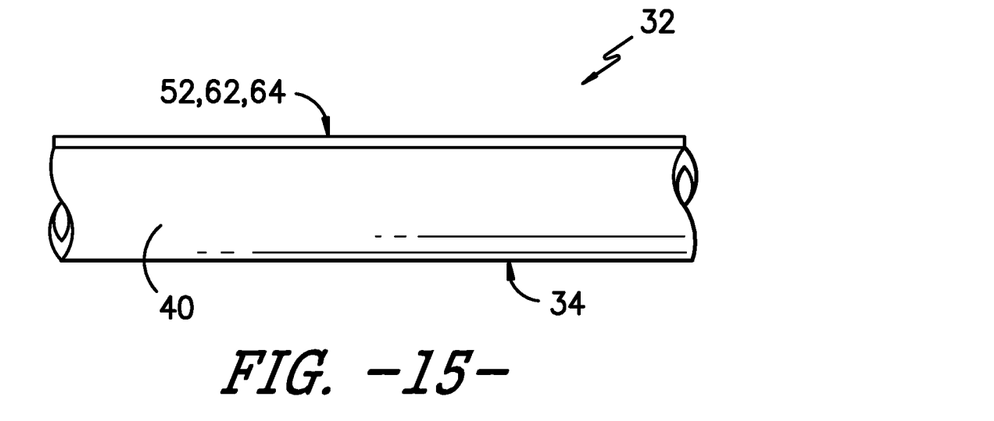
FIG. 15 illustrates a detailed view of a portion of the needle assembly according to the present disclosure, particularly illustrating a conduit assembly linearly mounted onto an exterior surface of the needle.
Figure 16:
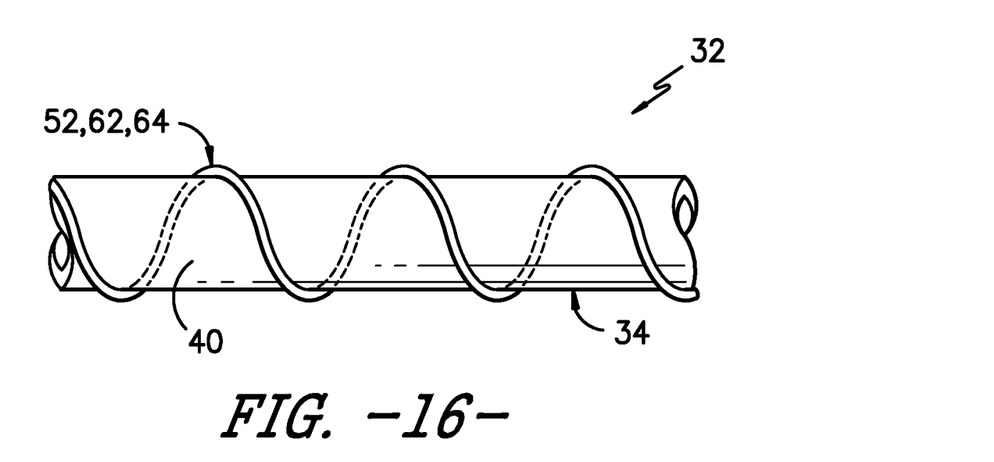
FIG. 16 illustrates a detailed view of a portion of the needle assembly according to the present disclosure, particularly illustrating a conduit assembly helically mounted onto an exterior surface of the needle.

Referring now to FIG. 15, the conductive traces 52 and/or the electrically-conductive cables 62, 64 may be arranged linearly or straight from the proximal end 36 to the distal end 38 of the needle 34. In alternative embodiments, as shown in FIG. 16, the conductive tracks 52 and/or the electrically-conductive cables 62, 64 may be arranged in a helical pattern from the proximal end 36 to the distal end 38 of the needle 40. In such embodiments, as shown, the conductive tracks 52 and/or the electrically-conductive cables 62, 64 electrically-conductive cables 62, 64 may be mounted onto the exterior surface 40 of the needle 34 in a twisted-pair configuration for improved common mode rejection ratio (CMRR) and/or reduced noise. Thus, the helical configurations are configured to create a periodic surface imperfection to provide increased tactility. It should be further understood that the flexible printed circuit board 46 and/or the electrical trace(s) 62 may be configured in a similar manner as shown in FIGS. 15 and 16.

Figure 17:
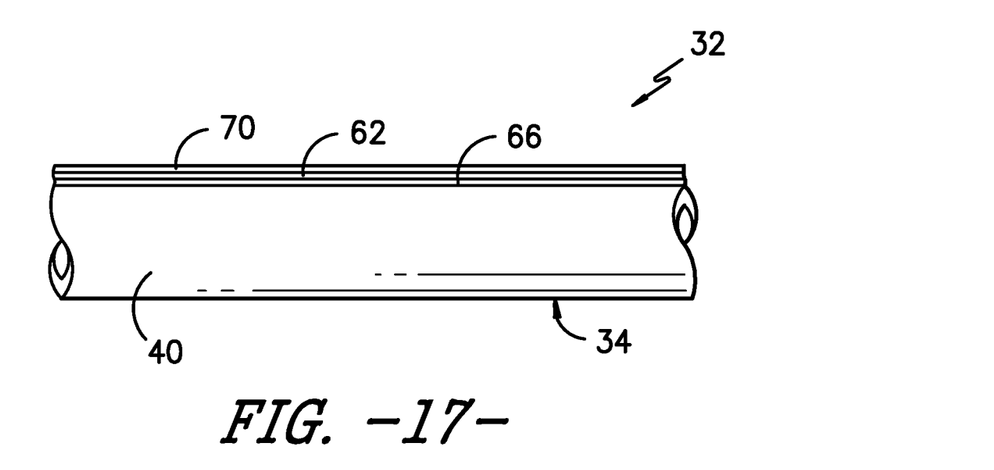
FIG. 17 illustrates a detailed view of a portion of the needle assembly according to the present disclosure, particularly illustrating an electrical trace printed onto an exterior surface of the needle via an additive manufacturing process.

Referring now to FIG. 17, a side view of yet another embodiment of a needle assembly 32 for the ultrasound imaging system 10 according the present disclosure is illustrated. As shown, the needle 34 of the needle assembly 32 may be coated, at least in part, of a first coating material 66. Further, as shown, the needle assembly 32 may include at least one electrical trace 68 printed onto the insulated portion of the needle 34 from the proximal end 36 to the distal end 38, e.g. via an additive manufacturing process. As such, the electrical trace(s) 68 are configured to electrically connect the needle transducer 30 to the power source 44. In addition, as shown, another insulating material 70 may be wrapped around the printed traces 68 so as to shield the electrical trace(s) 68 from the patient. Thus, in such embodiments, the needle 34 can be coated (such as sprayed and/or via a dipping process) with the insulating material 70 (such as polyimide) and the conductive electrical traces 68 can subsequently be placed over the insulation 66 (by deposition or conductive film, such as gold or copper). In addition, as mentioned, another insulation layer 70 can then be used to cover the electrical trace(s) 68 and the lower insulation layer 70. It should be further understood that the insulation layer(s) 66, 70 may also be used to insulate the flexible printed circuit board 46 and/or the cable(s) 62, 64 in a similar manner as shown in FIG. 17.

In certain embodiments, the additive manufacturing process may include, for example, of directed energy deposition, direct laser deposition, or any other suitable additive manufacturing technique. By using additive manufacturing, the electrical trace(s) 68 can be printed at the distal end 38 of the needle 34 in thin layers so as not to disturb the overall efficacy of the needle 34 in puncturing the necessary tissue of the patient. For example, in one embodiment, each of the electrical trace(s) 68 may have a predetermined thickness ranging from about 0.01 millimeters (mm) to about 0.05 mm. As used herein, terms of degree, such as "about," are meant to encompass a range of +/−10% from the value set forth.

It should also be understood that interconnection of the various electrical connections described herein (e.g. the flexible printed circuit board 46, the conduit assembly 58/cables 62, 64, and/or the electrical traces 68) and the needle transducer 30 can be achieved via a variety of methods. For example, in certain embodiments, the various electrical connections may be made via soldering and/or by using a conductive or non-conductive epoxy joint, i.e. with or without a polychlorinated biphenyl (PCB) interface, which can be used to wire bond to the device rather than connecting directly to the wire/cable.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An active needle assembly for use with an ultrasound imaging system, the needle assembly comprising:
   a needle comprising a proximal end and a distal end and defining an exterior curved surface comprising a cavity recessed within the needle and extending in a longitudinal direction along a length of the needle from the proximal end to the distal end of the needle, the cavity defining an embedded flat portion extending in the longitudinal direction at the distal end, the distal end adapted to be inserted into a patient;
   a needle transducer mounted within the cavity atop the embedded flat portion of the needle so as to not extend beyond an outer diameter of the needle; and
   a flexible printed circuit board on the exterior surface of the needle, the flexible printed circuit board comprising at least one conductive trace, the at least one conductive trace defining a width on the curved surface of the needle ranging from about 0.01 millimeters (mm) to about 0.25 mm, the flexible printed circuit board electrically connecting the needle transducer to a power source.

2. The needle assembly of claim 1, wherein the flexible printed circuit board comprises a flexible base with a plurality of conductive traces printed thereon, the at least one conductive trace being one of the plurality of conductive traces, the plurality of conductive traces comprises a first conductive trace configured to send signals from the needle transducer and a second conductive trace configured to receive signals from the ultrasound imaging system, the flexible base being mounted to the exterior curved surface of the needle.

3. The needle assembly of claim 2, wherein the plurality of conductive traces are printed on the flexible base via at least one screen printing, flexography, gravure printing, offset lithography, inkjet printing, or additive manufacturing.

4. The needle assembly of claim 1, wherein the needle transducer is mounted at the distal end of the needle.

5. The needle assembly of claim 1, further comprising at least one insulation layer positioned atop the flexible printed circuit board opposite the exterior curved surface of the needle so as to shield the flexible printed circuit board from the patient.

6. The needle assembly of claim 1, further comprising at least one insulation layer positioned between the flexible printed circuit board and the exterior curved surface of the needle.

7. The needle assembly of claim 2, wherein the plurality of conductive traces of the flexible printed circuit board are arranged linearly from the proximal end to the distal end of the needle.

8. The needle assembly of claim 2, wherein the plurality of conductive traces of the flexible printed circuit board are arranged in a helical pattern from the proximal end to the distal end of the needle.

9. A needle assembly for use with an ultrasound imaging system, the needle assembly comprising:
- a needle comprising a proximal end and a distal end, the distal end adapted to be inserted into a patient;
- a needle transducer mounted to an exterior surface of the needle at the distal end;
- a separate, conduit assembly mounted to a single side of the exterior surface of the needle from the proximal end of the needle and terminating before the distal end, the conduit assembly defining at least one tubing with at least one lumen therethrough, wherein the at least one lumen defines a diameter of up to about 0.25 millimeters (mm); and
- at least one electrically-conductive cable extending through the conduit assembly and electrically connecting the transducer to a power source,
- wherein the needle transducer is mounted distally of the conduit assembly on the exterior surface of the needle.

10. The needle assembly of claim 9, wherein the conduit assembly comprises at least one of metal tubing or polymer shrink tubing.

11. The needle assembly of claim 9, wherein the conduit assembly defines at least two lumens, and wherein each of the two lumens defines a diameter of up to about 0.25 mm.

12. The needle assembly of claim 9, wherein the conduit assembly is arranged linearly from the proximal end to the distal end of the needle.

13. The needle assembly of claim 9, wherein the at least one electrically-conductive cable comprises at least one of a single core wire or a coaxial cable.

14. A needle assembly for use with an ultrasound imaging system, the needle assembly comprising:
- a needle comprising a proximal end and a distal end and defining an exterior curved surface comprising a cavity recessed within the needle and extending in a longitudinal direction along a length of the needle from the proximal end to the distal end of the needle, the cavity defining an embedded flat portion extending in the longitudinal direction at the distal end, the distal end adapted to be inserted into a patient;
- a transducer mounted within the cavity atop the embedded flat portion of the needle at the distal end so as to not extend beyond an outer diameter of the needle; and
- at least one electrical trace printed on the exterior curved surface of the needle from the proximal end to the distal end via an additive manufacturing process, the at least one electrical trace defining a width on the curved surface of the needle ranging from about 0.01 millimeters (mm) to about 0.25 mm, the at least one electrical trace electrically connecting the transducer to a power source.

15. The needle assembly of claim 14, further comprising a plurality of electrical traces printed on the exterior curved surface of needle via the additive manufacturing process.

16. The needle assembly of claim 14, further comprising at least one insulation layer positioned atop the at least one electrical trace opposite the exterior curved surface of the needle so as to shield the at least one electrical trace from the patient.

17. The needle assembly of claim 14, further comprising at least one insulation layer positioned between the at least one electrical trace and the exterior curved surface of the needle.

18. The needle assembly of claim 14, wherein the at least one electrical trace is arranged linearly from the proximal end to the distal end of the needle or in a helical pattern from the proximal end to the distal end of the needle.

* * * * *